US00PP24696P2

(12) United States Plant Patent
NeSmith

(10) Patent No.: US PP24,696 P2
(45) Date of Patent: Jul. 29, 2014

(54) SOUTHERN HIGHBUSH BLUEBERRY PLANT NAMED 'TH-819'

(50) Latin Name: *Vaccinium corymbosum*
Varietal Denomination: TH-819

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 85 days.

(21) Appl. No.: 13/694,416

(22) Filed: Nov. 30, 2012

(51) Int. Cl.
*A01H 5/00* (2006.01)

(52) U.S. Cl.
USPC ..... Plt./157

(58) Field of Classification Search
CPC ..... A01H 1/00; A01H 1/04; A01H 1/06; A01H 4/00; A01H 4/05; A01H 4/008; A01H 5/08
USPC ..... Plt./157
See application file for complete search history.

*Primary Examiner* — Annette Para
(74) *Attorney, Agent, or Firm* — Klarquist Sparkman, LLP

(57) ABSTRACT

The variety 'TH-819' achieves 50% ripening in late April in southern Georgia. The new variety flowers relatively early, with the date of 50% flowering before the date of 50% flowering for 'Rebel' and 'Star'. 'TH-819' has good flavored berries and a berry size that is good, but typically smaller than the size of berries of 'Emerald'.

4 Drawing Sheets

Latin name of the genus and species of the plant claimed: 'TH-819' is mainly a *Vaccinium corymbosum* southern highbush blueberry plant with some *Vaccinium darrowii* in its pedigree.

Variety denomination: The new southern highbush blueberry plant claimed is a new variety denominated 'TH-819'.

BACKGROUND OF THE INVENTION

The present invention relates to the discovery of a new and distinct cultivar of southern highbush blueberry plant, hereinafter referred to as 'TH-819', as herein described and illustrated.

Southern highbush blueberries continue to gain a significant share of the production acreage of commercial blueberries in Georgia. One of the major interests in the species is early ripening berries, especially around the first of May or earlier in Georgia. The variety 'Star' (U.S. Plant Pat. No. 10,675) has dominated the market window due to its reliability and firm, early ripening flavorful berries. In 2006, the variety 'Rebel' (U.S. Plant Pat. No. 18,138) was released. 'Rebel' berries ripen earlier than berries of 'Star'. 'Rebel' has rapidly become very popular due to its early ripening fruit (around the last few days in April and the first week of May in South Georgia). In general, the earlier that berries ripen, the higher the price received for the berries. Thus, additional early ripening blueberry varieties are desired.

'TH-819' was first identified in 2001 growing in a cultivated area at the Georgia Experiment Station in Griffin, Ga., originating from a cross of 'Star'×'Bladen' (unpatented) made in 1998. Designated selection 'TH-819' in 2003, 'TH-819' was first asexually propagated in Griffin, Ga. by softwood cuttings for additional testing. Asexually propagated 'TH-819' plants, propagated by softwood cuttings, have been observed growing in Alapaha, Ga., in Ware County, Ga. and in Bacon County, Ga.

The new blueberry plant variety 'TH-819' has been shown to maintain its distinguishing characteristics through successive asexual propagations by softwood cuttings in Alapaha, Ga., Griffith, Ga., Ware County, Ga. and Bacon County, Ga. Plants from softwood cuttings have been directly planted in the ground.

The new blueberry plant variety 'TH-819' has not been observed under all possible environmental conditions. The phenotype may vary somewhat with variations in environment and cultural practices such as temperature and light intensity without, however, any variance in genotype.

The following traits of the new 'TH-819' variety have been repeatedly observed in Alapaha, Ga., Griffin, Ga., Ware County, Ga. and Bacon County, Ga., and have been determined to be the unique combination characteristics of the new southern highbush blueberry plant variety 'TH-819':

1. Early flowering;
2. Early ripening fruit;
3. Good fruit flavor;
4. Good fruit size.

The new variety 'TH-819' has been compared to the southern highbush blueberry varieties 'Emerald' (U.S. Plant Pat. No. 12,165), 'Rebel', and 'Star'.

COMPARISON TO OTHER VARIETIES

The new variety 'TH-819' is very early ripening, ripening before the early varieties 'Rebel' and 'Star' in South Georgia. 'TH-819' has medium to large berries with good flavor as compared to standards 'Emerald', 'Rebel' and 'Star' varieties growing at South Georgia test sites in the past 6 years (Tables 2 thru 4). No notable disease or other pest problems have been observed for the new variety that are not common for these standard varieties. However, 'TH-819' does flower very early (similar to 'Emerald') which can be problematic at times. Therefore, it would be expected that 'TH-819' would be grown with frost protection measures for more reliable production in growing areas where freezing is a risk. The new variety is estimated to have a chilling requirement of 300 to 400 hours or less below 45° F. (based on comparison of flowering dates with those of 'Emerald', 'Rebel' and 'Star' varieties.

As indicated previously (Tables 1-4), an outstanding feature of 'TH-819' is early ripening fruit. In all tests in south Georgia locations, 'TH-819' averaged ripening 7 to 12 days earlier than 'Star' and 'Rebel', and more than 2 weeks earlier than 'Emerald'. To give a more detailed view of ripening times, Table 4 depicts yearly data for the varieties being compared at the Alapaha Research Farm location over a multi-year period. The data reveal that, in each year, 'TH-819' consistently ripened earlier than any of the other three commercial varieties ('Emerald', 'Rebel' and 'Star'). The data are estimates of 50% ripening time, and typically berries will begin ripening (10% ripe fruit) 7 to 10 days earlier than this. Thus, with 'TH-819' there was harvestable fruit ready on plants in some years by April 15, which is a very early ripening time for South Georgia.

As mentioned previously, the early ripening berries of 'TH-819' are coupled with an early flowering time as well. Data from the 3 trials indicated that the fruit development period (FDP) of 'TH-819', 'Rebel', and 'Star' are similar and that 'TH-819' simply starts flowering earlier. This early flowering can result in freeze/frost issues during many years in South Georgia. Therefore, it is recommended that 'TH-819' be provided with freeze protection measures (e.g., overhead sprinkler frost protection) when possible. Early flowering has caused problems with growers of the variety 'Emerald' for years. Growers particularly become frustrated that, although 'Emerald' flowers early, it does not ripen early, thus there is little "reward" for the "risk" of growing the variety. However, the early ripening of 'TH-819' should offer growers a chance for higher market prices, thus, a "reward" for the "risk".

While the major attraction of 'TH-819' may be the early ripening fruit, the variety does have additional favorable attributes. In most evaluations, 'TH-819' tended to have the best flavor as compared to the other varieties, especially compared to 'Emerald', 'Rebel' and 'Star'. The bland flavor of 'Rebel' has been one of the biggest complaints against the variety. 'TH-819' fruit size is similar to 'Star' in most years, although, 'Rebel' and 'Emerald' berry size was most often larger. 'TH-819' also has a good fruit scar and firmness, and has good plant vigor.

While yields were not obtained in the trials, cropping estimates (related to yield) were made each year for the various trial entries. 'TH-819' cropping has been good, especially for an early flowering variety. Note that the Alapaha, Ga. site was not frost protected in any year, while the Ware County, Ga. site did have some frost protection and the Bacon County, Ga. site was frost protected each year. Thus, 'TH-819' has demonstrated good flower bud production and fruit set, both contributing to reasonable yield potential.

TABLE 1

5-year average ratings of some fruit and plant characteristics of 'TH-819' and southern highbush standard cultivars 'Emerald', 'Rebel', and 'Star' (2006-2011) in field test plots at Alapaha, GA. Rating scales are based on a 1 to 10 score, with 1 being the least desirable and 10 being the most desirable. These plants were established in 2004. A severe freeze in 2007 limited evaluations for that year. This was not a freeze protected site.

| Berry and Plant attributes [y] | Cultivar 'TH-819' | 'Emerald' | 'Rebel' | 'Star' |
|---|---|---|---|---|
| Berry size | 7.5 ± 0.2 | 8.6 ± 0.2 | 7.5 ± 0.2 | 7.7 ± 0.2 |
| Berry scar | 7.8 ± 0.2 | 7.8 ± 0.3 | 7.8 ± 0.2 | 7.5 ± 0.3 |
| Berry color | 7.7 ± 0.2 | 7.8 ± 0.3 | 7.2 ± 0.2 | 7.2 1 0.1 |
| Berry firmness | 7.5 ± 0.2 | 7.3 ± 0.2 | 7.6 ± 0.2 | 7.2 ± 0.2 |
| Berry flavor | 8.1 ± 0.3 | 7.0 ± 0.2 | 6.9 ± 0.1 | 7.2 ± 0.2 |
| Cropping | 6.1 ± 1.4 | 5.1 ± 1.1 | 7.5 ± 1.7 | 6.0 ± 1.6 |
| Plant vigor | 8.7 ± 0.5 | 7.0 ± 0.3 | 7.7 ± 0.4 | 8.6 ± 0.4 |
| Date of 50% flowering | Feb. 21 | Feb. 18 | Mar. 3 | Mar. 7 |
| Date of 50% ripening | April 24 | May 9 | May 3 | May 6 |
| Fruit development period (days) | 62 ± 2.0 | 80 ± 4.0 | 62 ± 2.0 | 62 ± 1.0 |

[y] Values are means ± the standard error with n = 5.

TABLE 2

5-year average ratings of some fruit and plant characteristics of 'TH-819' and southern highbush standard cultivars 'Emerald'. 'Rebel', and 'Star' (2005-2010) in field test plots at a test site in Ware County, GA. Rating scales are based on a 1 to 10 score, with 1 being the least desirable and 10 being the most desirable. These plants were established in 2004. This was a freeze protected site via overhead sprinklers.

| Berry and Plant attributes [y] | Cultivar 'TH-819' | 'Emerald' | 'Rebel' | 'Star' |
|---|---|---|---|---|
| Berry size | 7.6 ± 0.2 | 9.0 ± 0.3 | 8.3 ± 0.3 | 7.6 ± 0.2 |
| Berry scar | 7.3 ± 0.2 | 8.0 ± 0.2 | 8.4 ± 0.2 | 7.6 ± 0.3 |
| Berry color | 7.4 ± 0.2 | 8.0 ± 0.1 | 7.8 ± 0.1 | 7.2 ± 0.1 |
| Berry firmness | 7.5 ± 0.2 | 7.9 ± 0.1 | 8.1 ± 0.1 | 7.6 ± 0.3 |
| Berry flavor | 7.5 ± 0.3 | 7.2 ± 0.3 | 6.9 ± 0.1 | 7.4 ± 0.2 |
| Cropping | 5.3 ± 1.3 | 4.9 ± 1.3 | 6.7 ± 1.1 | 6.3 ± 0.6 |
| Plant vigor | 7.7 ± 0.1 | 8.9 ± 0.1 | 9.4 ± 0.3 | 8.1 ± 0.5 |
| Date of 50% flowering | Feb. 15 | Feb. 8 | Feb. 26 | Mar. 1 |
| Date of 50% ripening | April 26 | May 8 | May 2 | May 7 |
| Fruit development period (days) | 72 ± 3.9 | 89 ± 4.0 | 66 ± 2.2 | 67 ± 2.7 |

[y] Values are means ± the standard error with n = 5.

TABLE 3

3-year average ratings of some fruit and plant characteristics of 'TH-819' and southern highbush standard cultivars 'Emerald', 'Rebel', and 'Star' (2009-2010) in field test plots at a test site in Bacon County, GA. Rating scales are based on a 1 to 10 score, with 1 being the least desirable and 10 being the most desirable. These plants were established in 2007. This was a freeze protected site via overhead sprinklers.

| Berry and Plant attributes [y] | Cultivar 'TH-819' | 'Emerald' | 'Rebel' | 'Star' |
|---|---|---|---|---|
| Berry size | 7.5 ± 0.1 | 8.7 ± 0.3 | 8.2 ± 0.2 | 7.8 ± 0.2 |
| Berry scar | 7.3 ± 0.1 | 7.2 ± 0.2 | 8.0 ± 0.1 | 7.2 ± 0.2 |
| Berry color | 7.5 ± 0.1 | 7.8 ± 0.6 | 7.4 ± 0.3 | 7.2 ± 0.2 |
| Berry firmness | 7.3 ± 0.1 | 7.5 ± 0.3 | 7.9 ± 0.3 | 7.5 ± 0.3 |
| Berry flavor | 7.7 ± 0.2 | 7.1 ± 0.4 | 6.8 ± 0.1 | 7.0 ± 0.1 |
| Cropping | 6.5 ± 0.7 | 6.3 ± 0.8 | 7.3 ± 0.4 | 6.0 ± 0.5 |
| Plant vigor | 9.3 ± 0.3 | 8.8 ± 0.6 | 9.6 ± 0.3 | 8.8 ± 0.2 |

TABLE 3-continued 3-year average ratings of some fruit and plant characteristics of 'TH-819' and southern highbush standard cultivars 'Emerald', 'Rebel', and 'Star' (2009-2010) in field test plots at a test site in Bacon County, GA. Rating scales are based on a 1 to 10 score, with 1 being the least desirable and 10 being the most desirable. These plants were established in 2007. This was a freeze protected site via overhead sprinklers.

| Berry and Plant attributes [y/] | Cultivar 'TH-819' | 'Emerald' | 'Rebel' | 'Star' |
|---|---|---|---|---|
| Date of 50% flowering | Mar. 7 | Mar. 8 | Mar. 12 | Mar. 16 |
| Date of 50% ripening | April 29 | May 14 | May 7 | May 10 |
| Fruit development period (days) | 56 ± 2.0 | 68 ± 2.4 | 59 ± 1.8 | 57 ± 2.0 |

[y/] Values are means ± the standard error with n = 3.

TABLE 4

Date of 50% ripening time for 'TH-819' and three standard ('Emerald', 'Rebel' and 'Star') southern highbush blueberry varieties at the Alapaha, GA Research Farm during 2006 through 2011. Note that a severe freeze in 2007 resulted in lost evaluations during that year.

| Year | Cultivar 'TH-819' | 'Emerald' | 'Rebel' | 'Star' |
|---|---|---|---|---|
| 2006 | April 22 | May 3 | May 1 | May 3 |
| 2008 | April 19 | May 8 | April 29 | May 6 |
| 2009 | April 23 | May 8 | April 28 | May 1 |
| 2010 | May 4 | May 19 | May 11 | May 15 |
| 2011 | April 24 | May 9 | May 6 | May 7 |

BRIEF DESCRIPTION OF THE FIGURES

The accompanying photographic illustrations show typical specimens in full color of the foliage and fruit of the new variety 'TH-819'. The colors are as nearly true as is reasonably possible in a color representation of this type. The colors of an illustration of this type may vary with lighting and other conditions. Therefore, color characteristics of this new variety should be determined with reference to the observations described herein, rather than from these illustrations alone.

BOTANICAL DESCRIPTION

Figure 1:
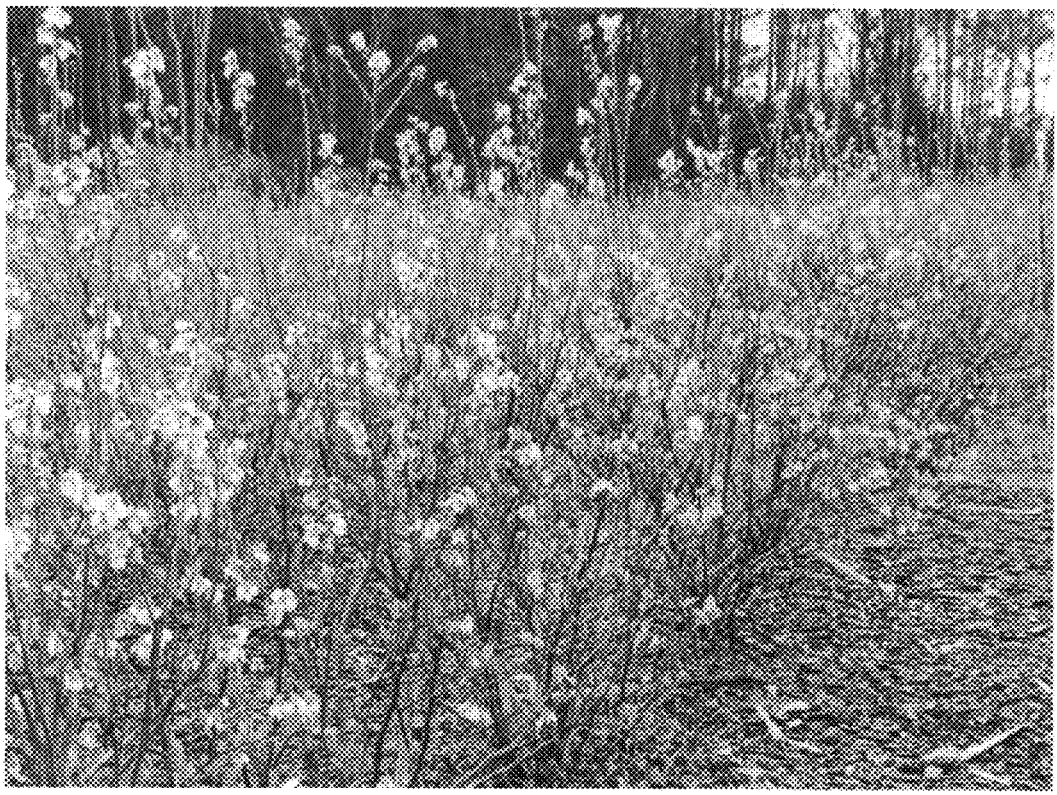
FIG. 1 is a photograph of typical three year old plants of the new variety 'TH-819' growing in Bacon County, Ga.
Figure 2:
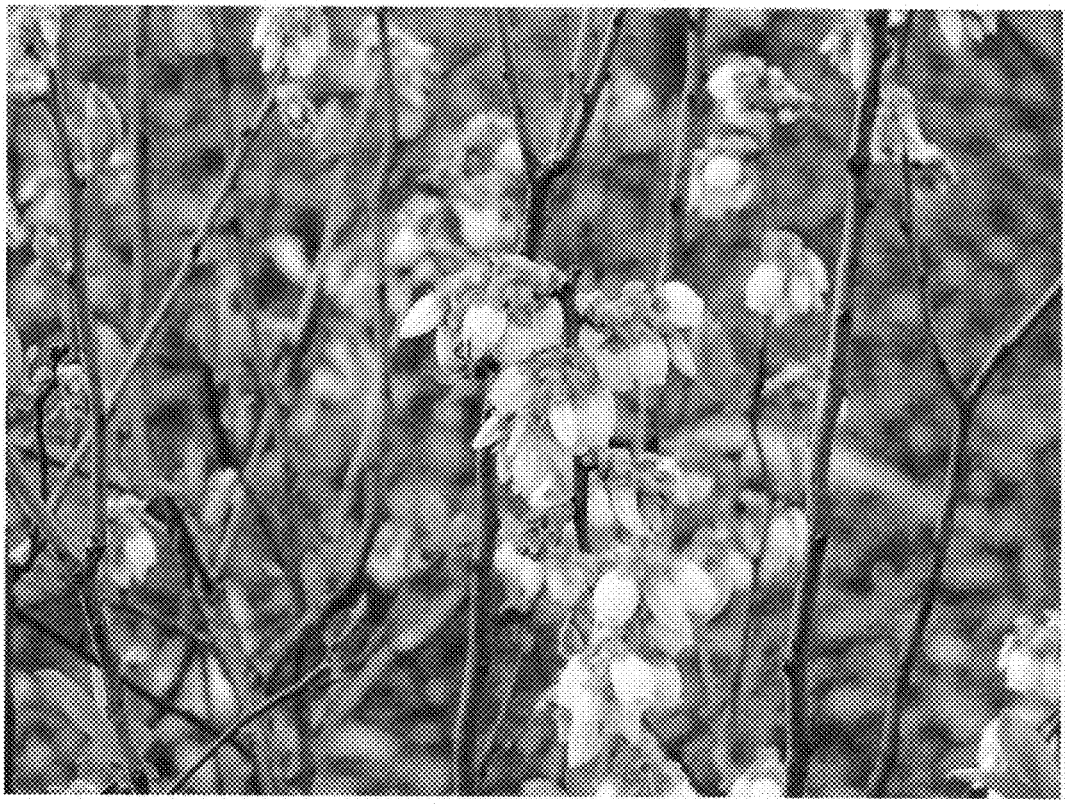
FIG. 2 is a close-up photograph of typical flowers of the new variety 'TH-819'.
Figure 3:
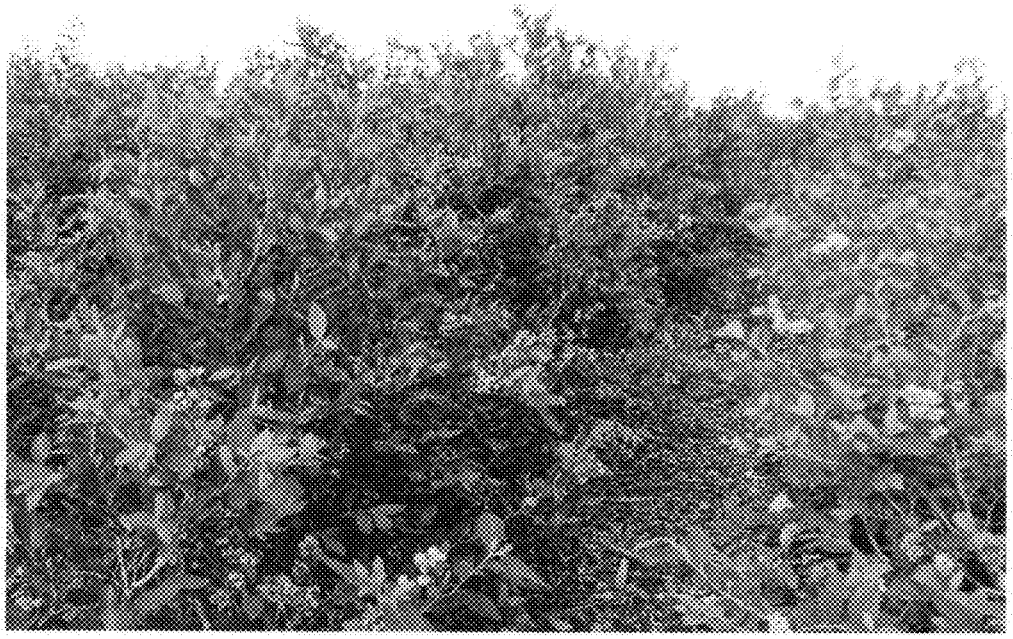
FIG. 3 is a photograph of three year old plants of the new variety 'TH-819' growing in Bacon County, Ga. during fruit ripening.
Figure 4:
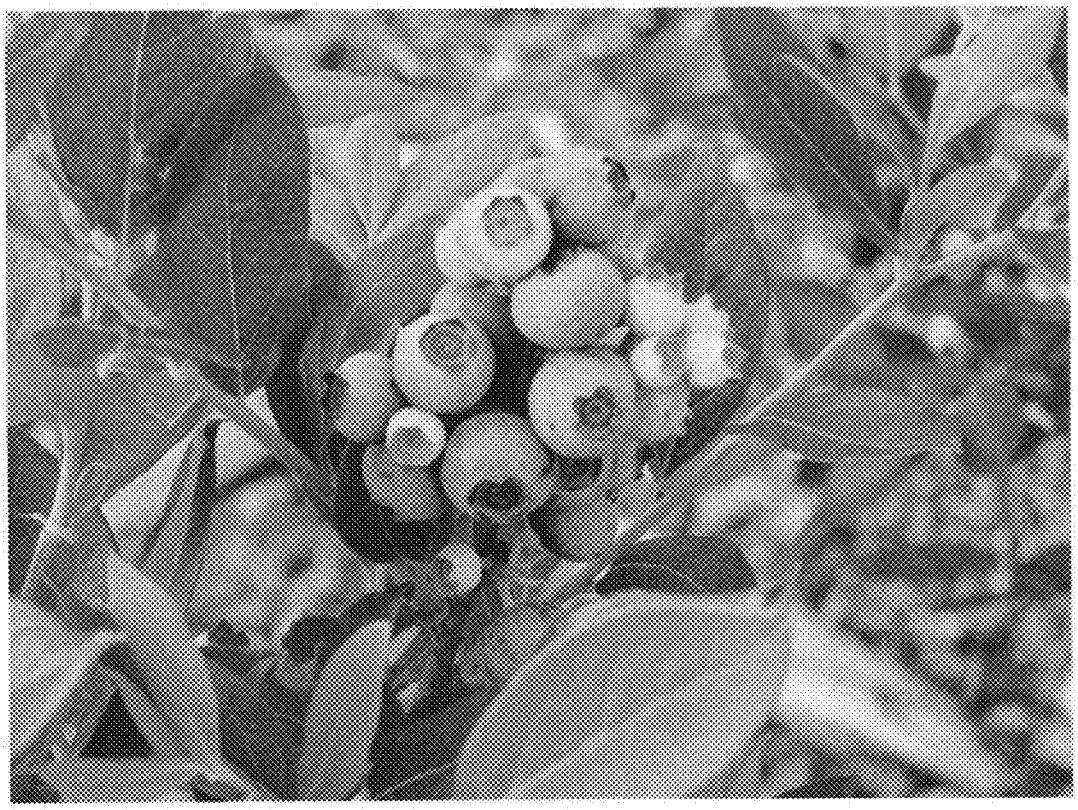
FIG. 4 is a close-up of 'TH-819' fruit.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and pomological characteristics of the new variety 'TH-819'. Where dimensions, sizes, colors, and other characteristics are given, it is to be understood that such characteristics are approximations and averages set forth as accurately as practicable. Color data are presented in Royal Horticultural Society Colour Chart (5$^{th}$ Edition) designations. The descriptions reported herein are largely from specimen plants grown in Alapaha, Ga. and Griffin, Ga., with supplemental irrigation. Plants were 3 to 6 years old.

Plant:

*Size*.—1.2 to 1.6 m tall by 3 years. Plants grown under highly productive soil and fertility conditions have exceeded 2.0 m tall in 4 years. The plant crown, or base, is narrow, typically 25 to 30 cm in diameter. The upper portion of plant canopy exceeds 1.0 m in diameter by 3 to 4 years.

*Growth habit*.—Upright, with 2 to 4 main canes arising from the crown, and multiple branching of shoots from those canes above ground.

*Growth*.—Plants are highly vigorous.

*Productivity*.—Medium to high crop/yield. Yields of 6 to 8 lbs per plant each year on plants 3 years old or older grown under well fertilized and irrigated field conditions.

*Cold hardiness*.—Similar to southern highbush varieties 'Star' and 'Rebel'.

*Chilling requirement*.—Plants require less than 400 hours of temperatures at or below 7° C. to induce normal leafing and flowering during the spring. The chill requirement is less than either the male parent 'Bladen' (non-patented variety; 700 plus hours of chilling required) or the female parent 'Star' (400 to 500 hours of chilling required).

*Leafing*.—Plants tend to break sufficient leaf buds simultaneously with, or shortly after, anthesis.

*Canes*.—Main cane base diameter 20 to 30 mm, color most near Grey 201A to Grey 201C; two year old cane diameter 8 to 16 mm, color transitioning from Yellow Green 145A to Greyed Orange 177B; current season wood diameter 3 to 6 mm, color Yellow Green 145A.

*Fruiting wood*.—Moderate number of twigs 10 to 15 cm in length, with internode lengths of 15 to 25 mm common.

*Disease resistance*.—No exceptional disease resistance or susceptibility observed. Typical for early season southern highbush varieties 'Star' and 'Rebel'.

Foliage:

*Leaf color*.—Healthy mature leaves: top side of leaf color is Green 137A to 137B, under side of leaf color is Yellow Green 147B to 147C.

*Leaf arrangement*.—Alternate, simple.

*Leaf shape*.—Elliptic.

*Leaf margins*.—Nearly entire.

*Leaf venation*.—Reticulate.

*Leaf apices*.—Broadly acuminate.

*Leaf bases*.—Acute.

*Leaf dimensions*.—Length: 50 to 65 mm; width: 20 to 35 mm.

*Petioles*.—Small, 3 to 5 mm long, 1.0 to 1.5 mm wide; Color: Yellow Green 145C.

*Leaf margins*.—Smooth.

*Leaf surface*.—Glaucous.

Flowers:

*Date of* 50% *anthesis*.—5-year average February 15 to February 21 in southeast Georgia.

*Flower shape*.—Urceolate.

*Flower bud number*.—Very high, averaging 6 to 8 buds per fruiting shoot.

*Flowers per cluster*.—4 to 7.

*Flower fragrance*.—None noticed.

*Corolla color*.—White NN155C.

*Corolla length.*—8.5 to 10.0 mm.
*Corolla width.*—7.0 to 7.5 mm.
*Corolla aperture width.*—4.0 to 4.5 mm.
*Flower peduncle.*—Length 8.0 to 12.0 mm; Color: Yellow Green 145C.
*Flower pedicel.*—Length 3.0 to 4.5 mm; Color: Green 138C.
*Calyx* (*with sepals*).—Diameter: 6.5 to 7.5 mm; Color: Green 137C.
*Stamen.*—Length: 6.5 to 7.0 mm; number per flower: 10; filament color: Yellow Green 145D.
*Style.*—Length: 8.0 to 10.0 mm; Color: Yellow Green 145B.
*Pistil.*—Length: 10.0 to 12.0 mm; ovary color: Green 138B.
*Anther.*—Length: 3.8 to 4.2 mm; number: 10; Color: Greyed Orange 166D.
*Pollen.*—Abundance: medium to high; Color: Yellow Orange 20C. 'TH-819' has a moderate degree of self-compatibility.

Fruit:

*Date of* 50% *maturity.*—5-year average April 24 to 26 in southeast Georgia.
*Fruit development period.*—62 to 72 days.
*Berry color.*—With wax Violet Blue 98D; with wax removed Black 202A.
*Berry flesh color.*—Yellow Green 145C.
*Berry surface wax abundance.*—Medium to high.
*Berry weight.*—$1^{st}$ harvest: 1.6 g to 1.8 g; $2^{nd}$ harvest 1.4 g to 1.6 g.
*Berry size.*—Height from calyx to scar: 13 to 14 mm; diameter: 15 to 17 mm.
*Berry shape.*—Semi-spherical.
*Fruit stem scar.*—Small to medium, dry, with little or no tearing upon harvest.
*Berry firmness.*—Moderately firm to firm.
*Berry flavor and texture.*—Sweet mildly acidic flavor; smooth texture.
*Storage quality.*—Good to very good.
*Suitability for mechanical harvesting.*—Likely suitable.
*Uses.*—Can be used as fresh fruit for shipping, for customer-pick and processing markets.

Seed:

*Seed abundance in fruit.*—Low, with less than 10 fully developed seeds per berry.
*Seed color.*—Greyed Orange 165A to 165B.
*Seed dry weight.*—40.6 mg per 100 seed.
*Seed size.*—1.5 to 2.0 mm long.

What is claimed is:

1. A new and distinct variety of southern highbush blueberry plant named 'TH-819', substantially as illustrated and described herein.

* * * * *